US00PP36500P2

(12) United States Plant Patent
Schoone

(10) Patent No.: US PP36,500 P2
(45) Date of Patent: Feb. 25, 2025

(54) ***PHALAENOPSIS* PLANT NAMED 'Snazzy'**

(50) Latin Name: *Phalaenopsis hybrida*
Varietal Denomination: Snazzy

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/826,078

(22) Filed: Sep. 5, 2024

Related U.S. Application Data

(60) Provisional application No. 63/539,328, filed on Sep. 20, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Snazzy', characterized by its upright and compact plant habit; moderately vigorous growth habit; strong flowering stems; strong leaves; freely flowering habit with typically two inflorescences developing per plant, each inflorescence with numerous flowers; salmon orange-colored flowers variably tinged with light purple; and good postproduction longevity.

2 Drawing Sheets

Figure 1:
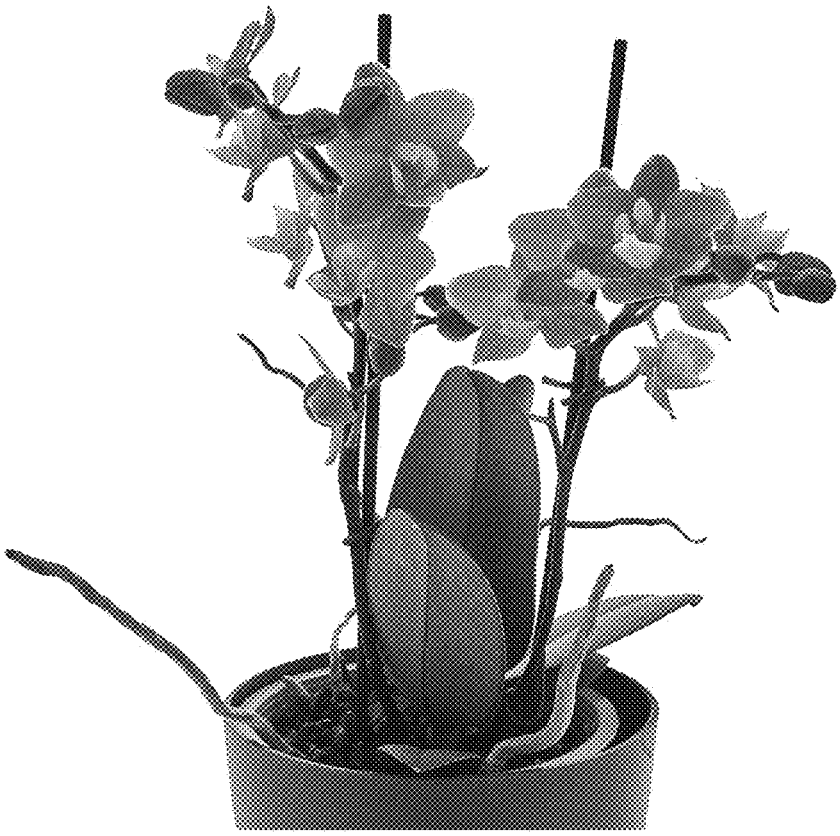

Botanical designation: *Phalaenopsis hybrida.*
Cultivar denomination: 'SNAZZY'.

CROSS-REFERENCED TO CLOSELY-RELATED APPLICATIONS

A European Community Plant Breeder's Rights application for the instant plant was filed by the Applicant/Assignee of the instant application, Floricultura B. V. of Heemskerk, The Netherlands on Jul. 25, 2023, application number 2023/1566. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Snazzy'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2013 in Assendelft, The Netherlands of a proprietary selection of *Phalaenopsis hybrida* 'Tying Shin Cupid' x 'Caribbean Sunset', not patented, as the female, or seed, parent with *Phalaenopsis hybrida* 'Pinlong Cheris', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February 2020.

Asexual reproduction of the new *Phalaenopsis* plant by in vitro meristem propagation in a controlled environment in Assendelft, The Netherlands since February 2021 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Snazzy'. These characteristics in combination distinguish 'Snazzy' as a new and distinct *Phalaenopsis* plant:

1. Upright and compact plant habit.
2. Moderately vigorous growth habit.
3. Strong flowering stems.
4. Strong leaves.
5. Freely flowering habit with typically two inflorescences developing per plant, each inflorescence with numerous flowers.
6. Salmon orange-colored flowers variably tinged with light purple.
7. Good postproduction longevity.

Plants of the new *Phalaenopsis* can be compared to plants of the female parent selection. Plants of the new *Phalaenopsis* differ primarily from plants of the female parent selection in flower color as flowers of plants of the new *Phalaenopsis* are salmon orange variably tinged with light purple in color whereas flowers of plants of the female parent selection are violet in color.

Plants of the new *Phalaenopsis* can be compared to plants of the male parent, 'Pinlong Cheris'. Plants of the new *Phalaenopsis* differ primarily from plants of 'Pinlong Cheris' in flower color as flowers of plants of the new *Phalaenopsis* are salmon orange variably tinged with light purple in color whereas flowers of plants of 'Pinlong Cheris' are soft violet in color.

Plants of the new *Phalaenopsis* can be compared to plants of *Phalaenopsis hybrida* 'Matchlight', not patented. In side-by-side comparisons, plants of the new *Phalaenopsis* differ primarily from plants of 'Matchlight' in plant habit as plants of the new *Phalaenopsis* are not as compact as plants of 'Matchlight'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Snazzy' grown in a container.

Figure 2:
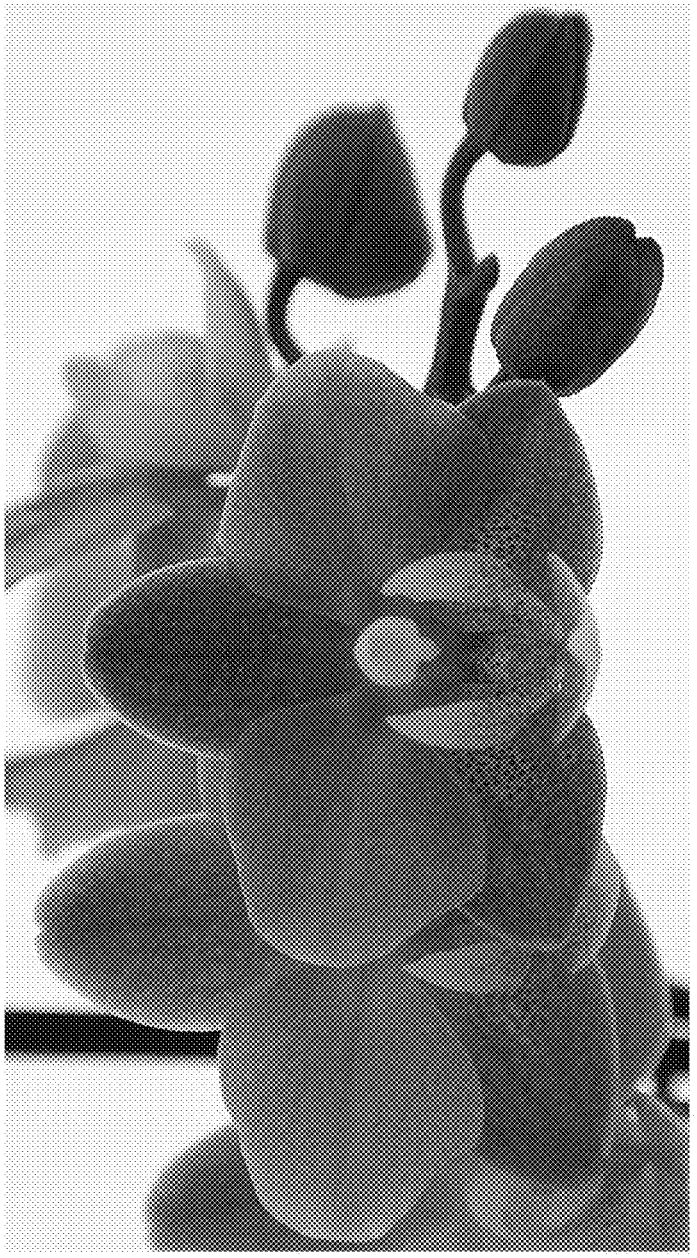

The photograph on the second sheet (FIG. 2) is a close-up view of typical flowers and flower buds of 'Snazzy'.

DETAILED BOTANICAL DESCRIPTION

The aforementioned photographs and following observations and measurements describe plants grown during the early spring in 11-cm containers in a glass-covered greenhouse in Heemskerk, The Netherlands and under cultural practices typically used in commercial *Phalaenopsis* production. Plants were 16 months old when the photographs and description were taken. During the first twelve months of production of the plants, day and night temperatures averaged 27° C. During the final four months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Snazzy'.

Parentage:

*Female, or seed, parent.*—Proprietary selection of *Phalaenopsis hybrida* 'Tying Shin Cupid' x 'Caribbean Sunset', not patented.

*Male, or pollen, parent.*—*Phalaenopsis hybrida* 'Pinlong Cheris', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 18 to 20 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright and compact plant habit with typically two inflorescences developing per plant, each inflorescence with numerous flowers; monopodial; moderately vigorous growth habit and moderate growth rate.

*Plant height, substrate level to top of foliar plane.*—About 10.3 cm.

*Plant height, substrate level to top of floral plane.*—About 19 cm.

*Plant diameter or spread.*—About 19.3 cm.

Leaf description:

*Arrangement and quantity.*—Distichous, simple; sessile; about three fully-developed leaves per plant.

*Length.*—About 11.7 cm.

*Width.*—About 5.1 cm.

*Aspect.*—Erect to slightly outwardly arching.

*Shape.*—Elliptic; slightly carinate and slightly convex.

*Apex.*—Unequal and broadly acute.

*Base.*—Sheathing. Sheath length: About 1.4 cm. Sheath width: About 8 mm. Sheath color, upper and lower surfaces: Close to 146C; towards the margins, tinged with close to N186C.

*Margin.*—Entire.

*Texture and luster, upper surface.*—Smooth, glabrous; slightly glossy.

*Venation pattern.*—Camptodromous.

*Color.*—Developing leaves, upper surface: Close to NN137A and NN137B. Developing leaves, lower surface: Close to 148A tinged with close to N186B; main vein, close to N186B. Fully expanded leaves, upper surface: Close to NN137A, NN137B and 137B; venation, close to 139A. Fully expanded leaves, lower surface: Close to 146B; towards the margins, close to N186C; venation, close to a blend of N186C and 200A.

Inflorescence description:

*Appearance and flowering habit.*—Showy zygomorphic flowers arranged on axillary simple or branched racemes; typically two inflorescences develop per plant; each inflorescence with about 13 flowers; flowers face outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about five months after planting; plants flower naturally during the winter into the spring.

*Flower longevity.*—Long flowering period, individual flowers maintain good substance for about six weeks on the plant; flowers not persistent.

*Inflorescence length (lowermost flower to inflorescence apex).*—About 12.7 cm.

*Inflorescence width.*—About 8.4 cm.

*Flower buds.*—Height: About 1.3 cm. Diameter: About 8 mm by 12 mm. Shape: Broadly ovate. Color: Close to 178A finely blotched with close to 195B; lower surface, close to 146C slightly tinged with close to 178A.

*Flower size*.—About 3.7 cm (vertical) by 4.2 cm (horizontal).

*Flower depth*.—About 2.2 cm.

*Petals, quantity and arrangement*.—Three, two lateral petals and one center petal transformed into a labellum.

*Lateral petals*.—Length: About 2 cm. Width: About 1.9 cm. Shape: Broadly ovate-rhomboidal. Apex: Obtuse. Margin: Entire. Texture and luster, upper and lower surfaces: Smooth, glabrous; moderately velvety; matte. Color: When opening, upper surface: Close to 161A; towards the top, close to 160A; densely covered with fine dots, close to 184A and 184B; main vein, close to 186A. When opening, lower surface: Close to 177C and 177D; towards the top, close to 148D; strongly tinged with close to 194A; main vein, tinged with close to 184C. Fully opened, upper surface: Close to 154C; towards the top, close to 154B; densely covered with close to fine dots, close to 179B and 179C; at the base, close to 84C; colors do not change with subsequent development. Fully opened, lower surface: Close to N170C and N170D; upper marginal edges, close to 11A; at the base, close to 84C; main vein, close to 84B; colors do not change with subsequent development.

*Labella*.—Appearance: Three-parted with two lateral lobes and a central lobe. Length, lateral lobes: About 1.1 cm. Width, lateral lobes: About 7 mm. Length, central lobe: About 1.6 cm. Width, central lobe: About 0.3 cm to 1.2 cm. Shape, lateral lobes: Obovate. Shape, central lobe: Rhomboidal with a slightly elongated apex. Apex, lateral lobes: Obtuse. Apex, central lobe: Emarginate. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 3 mm in width and about 2 mm in height. Color: When opening, upper surface: Lateral lobes: Close to NN155D; lower margins, close to 4C and 4D; at the base, close to 4C and 4D; lower ⅔'s of the lobe, axial stripes and dots, close to 183B. Central lobe: Close to 154B densely covered with fine dots, close to 184A to 184C; towards the top, close to 150D; at the base, close to 4D with radial stripes and dots, close to 184D. When opening, lower surface: Lateral lobes: Close to NN155D; lower margins and at the base, close to 5D. Central lobe: Close to 160C; towards the top, close to 150D; margins, sparsely covered with dots, close to 165A; at the base, close to 160C and 160D; main vein, tinged with close to 84C. Fully opened, upper surface: Lateral lobes: Close to NN155D; lower margins and at the base, close to 12B and 12C; lower ⅔'s of the lobe with axial stripes and dots, close to 183B. Central lobe: Close to 13B densely covered with fine dots, close to 184B to 184C; towards the top, close to 150D; at the base, close to 4D with radial stripes and dots, close to 184D. Fully opened, lower surface: Lateral lobes: Close to NN155D; lower margins and at the base, close to 5D. Central lobe: Close to 162C; towards the top, close to 150D; towards the margins, close to 13B and sparsely covered with dots, close to 165B and 165C; at the base, close to 155A; main vein, tinged with close to 84C. Callosities: When developing: Close to 3D; towards the top, close to 9B with fine dots, close to 183A. Fully developed: Close to 3C; towards the top, close to 12B with fine dots, close to 183A.

*Sepals*.—Quantity and arrangement: Three, one upper dorsal sepal and two lower lateral sepals. Length, dorsal sepal: About 2.1 cm. Width, dorsal sepal: About 1.5 cm. Length, lateral sepals: About 2.1 cm. Width, lateral sepals: About 1.6 cm. Shape, dorsal sepal: Elliptic. Shape, lateral sepals: Ovate. Apex, dorsal sepal: Shallowly emarginate. Apex, lateral sepals: Acute. Base, dorsal and lateral sepals: Cuneate. Margins, dorsal sepal: Entire; not undulate. Margins, lateral sepals: Entire; mostly not undulate except for lower margins which are slightly and coarsely undulate. Texture and luster, dorsal and lateral sepals, upper and lower surfaces: Smooth, glabrous; moderately velvety; matte. Color, dorsal sepal: When opening, upper surface: Close to 183D moderately covered with fine dots, close to 151B; main vein, tinged with close to N186D. When opening, lower surface: Close to 177B; towards the margins and top, close to 178A and 178B; moderately covered with fine dots, close to 151B. Fully opened, upper surface: Close to 179B; towards the top, close to 180B; moderately covered with fine dots, close to 154C; marginal edges, close to 160B. Fully opened, lower surface: Close to 182B flushed with close to 153D; narrow marginal edges, close to 160B; at the base, close to 186B. Color, lateral sepals: When opening, upper surface: Upper half, close to 183D; lower half, close to 176B and 176C; center, close to 151B with fine dots, close to 183A. When opening, lower surface: Close to 152D tinged with close to 176B; venation, close to 176B. Fully opened, upper surface: Close to 153D; towards the lower margin, flushed with close to 173B; towards the upper margin and top, flushed with close to 180B; center, heavily covered with fine dots, close to 184A; at the base, close to 186B. Fully opened, lower surface: Close to 180D; towards the top, close to 181A and 182A; strongly tinged with close to 153A; main vein, close to 184B.

*Peduncles*.—Length: About 19.2 cm. Diameter: About 4 mm. Strength: Strong. Aspect: Upright to outwardly arching. Texture and luster: Smooth, glabrous; matte. Color: Close to 200A moderately covered with fine dots, close to 147D.

*Pedicels*.—Length: About 2.5 cm. Diameter: About 2.5 mm. Strength: Moderately strong. Aspect: About 60° from peduncle axis. Texture and luster: Smooth, glabrous; matte. Color: Close to 179B and 179C; proximal end, close to 200B and distal end, close to 72B.

*Reproductive organs*.—Androecium: Column length: About 8 mm. Column width: About 4 mm. Column color: Close to 76C and 76D. Pollinia quantity: Two. Pollinia diameter (per two pollinia): About 1.5 mm. Pollinia color: Close to 17B. Gynoecium: Stigma length: About 2 mm. Stigma width: About 3 mm. Stigma shape: Reniform. Stigma color: Close to N155A. Ovary length: About 6 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Snazzy' as herein illustrated and described.

* * * * *